United States Patent
Harding

(10) Patent No.: US 11,744,997 B2
(45) Date of Patent: *Sep. 5, 2023

(54) INTRODUCER NEEDLE WITH NOTCHES FOR IMPROVED FLASHBACK

(71) Applicant: Becton, Dickinson and Company, Franklin Lakes, NJ (US)

(72) Inventor: Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/718,587

(22) Filed: Apr. 12, 2022

(65) Prior Publication Data

US 2022/0233823 A1     Jul. 28, 2022

Related U.S. Application Data

(63) Continuation of application No. 16/725,704, filed on Dec. 23, 2019, now Pat. No. 11,324,926, which is a (Continued)

(51) Int. Cl.
*A61M 25/06*     (2006.01)

(52) U.S. Cl.
CPC .... *A61M 25/0606* (2013.01); *A61M 25/0693* (2013.01)

(58) Field of Classification Search
CPC .............. A61M 25/06; A61M 25/0606; A61M 25/0612; A61M 25/0693; A61M 25/065;
(Continued)

(56) References Cited

U.S. PATENT DOCUMENTS

| 4,046,144 A | 9/1977 | McFarlane |
| 5,810,780 A | 9/1998 | Brimhall et al. |

(Continued)

FOREIGN PATENT DOCUMENTS

| DE | 69406333 | 2/1998 |
| EP | 0806221 | 11/1997 |

(Continued)

*Primary Examiner* — Kami A Bosworth
*Assistant Examiner* — Antarius S Daniel
(74) *Attorney, Agent, or Firm* — KIRTON MCCONKIE; Whitney Blair; Kevin Stinger

(57) ABSTRACT

A catheter system may include a catheter adapter, a catheter extending distally from the catheter adapter, an introducer needle extending through the catheter, a flash chamber in fluid communication with a needle lumen of the introducer needle, and a seal element. The introducer needle may include a wall defining the needle lumen, a first notch formed through the wall, and a second notch formed through the wall. The seal element may be proximal to the first notch and the second notch and within the catheter between an outer surface of the introducer needle and an inner surface of the catheter. The seal element may prevent priming fluid from travelling distal to the seal element. The seal element in conjunction with the first notch, the second notch, and the flash chamber may facilitate pressure-driven blood flow into the catheter for detection of flashback and transfixing when priming occurs prior to insertion into vasculature.

8 Claims, 12 Drawing Sheets

Related U.S. Application Data continuation-in-part of application No. 15/946,593, filed on Apr. 5, 2018, now Pat. No. 10,869,993.

(58) Field of Classification Search
CPC .......... A61M 25/0028; A61M 25/0029; A61M 25/003; A61M 25/0032; A61M 2005/3112; A61M 5/158; A61M 2025/0004; A61M 2025/0006; A61M 2025/0018; A61M 2025/0039; A61M 2025/0073

See application file for complete search history.

(56) References Cited

U.S. PATENT DOCUMENTS

| | | | | |
|---|---|---|---|---|
| 7,670,317 | B2 * | 3/2010 | Cindrich | ........... A61M 39/0606 |
| | | | | 604/167.01 |
| 2003/0153874 | A1 | 8/2003 | Tal | |
| 2010/0168675 | A1 | 7/2010 | Cindrich et al. | |
| 2011/0313357 | A1 * | 12/2011 | Skutnik | ............. A61M 25/0009 |
| | | | | 264/254 |
| 2012/0016296 | A1 | 1/2012 | Charles | |
| 2013/0261554 | A1 * | 10/2013 | Baid | ................. A61M 25/0606 |
| | | | | 604/164.06 |
| 2014/0081210 | A1 | 3/2014 | Bierman et al. | |
| 2015/0202422 | A1 * | 7/2015 | Ma | .................... A61M 39/0693 |
| | | | | 604/167.02 |
| 2017/0120001 | A1 | 5/2017 | Hyer et al. | |
| 2017/0239443 | A1 | 8/2017 | Abitabilo et al. | |
| 2020/0237278 | A1 | 7/2020 | Asbaghi | |

FOREIGN PATENT DOCUMENTS

| | | |
|---|---|---|
| EP | 2260897 | 12/2010 |
| JP | H10-033686 | 2/1998 |
| JP | 2012517326 | 8/2012 |
| JP | 2016511083 | 4/2016 |
| WO | 2017074683 | 5/2017 |

* cited by examiner

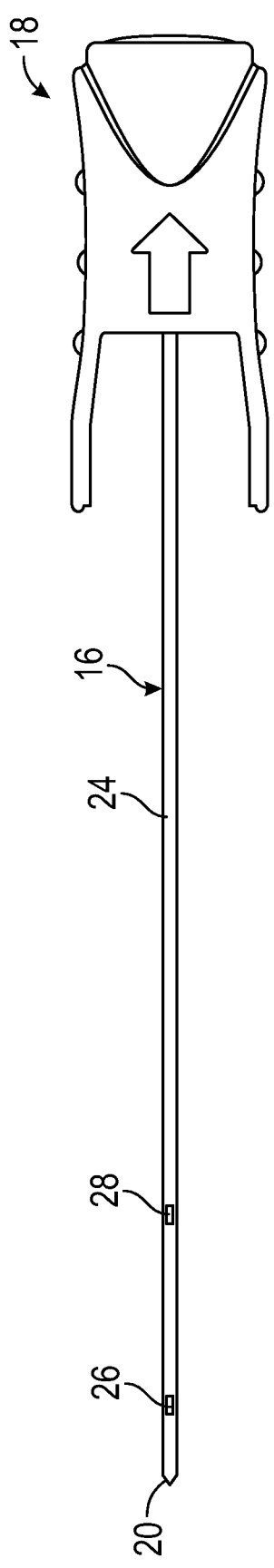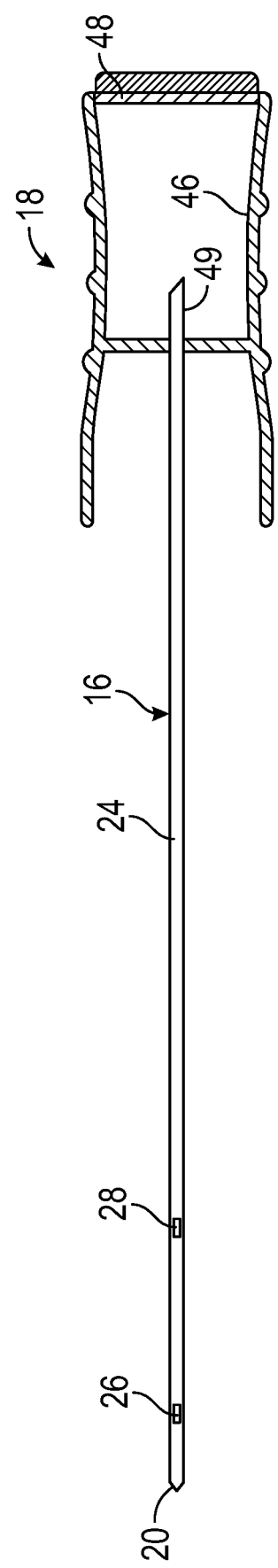
FIG. 3A
FIG. 3B

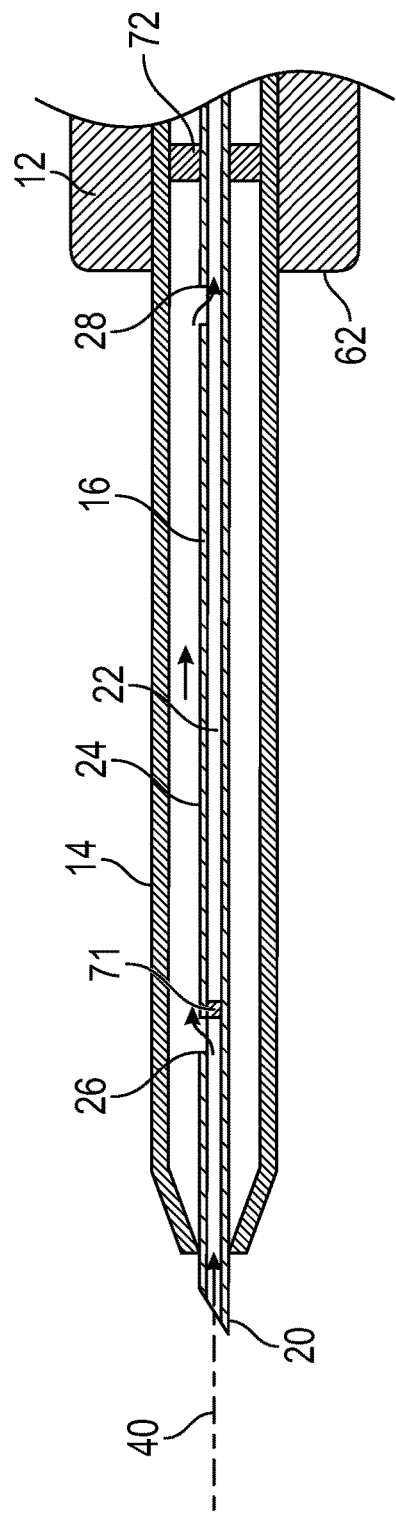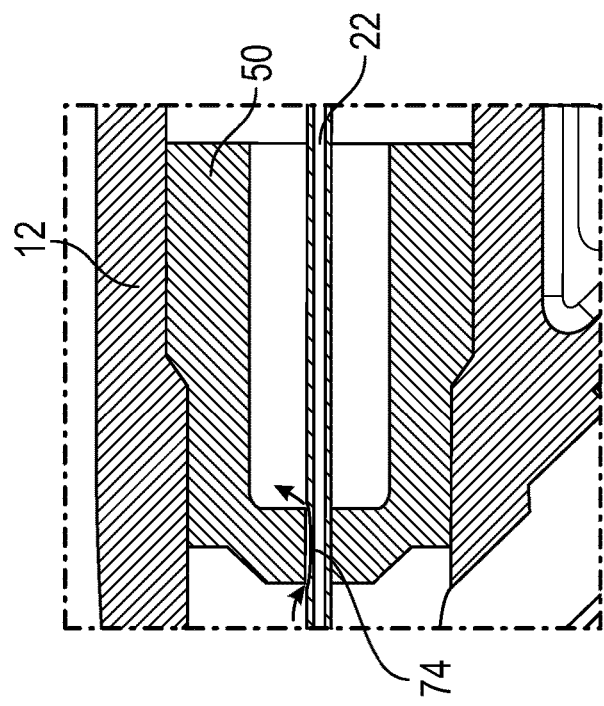
FIG. 5B
FIG. 5C

INTRODUCER NEEDLE WITH NOTCHES FOR IMPROVED FLASHBACK

CROSS-REFERENCE TO RELATED APPLICATION

This application is a continuation of U.S. patent application Ser. No. 16/725,704, filed Dec. 23, 2019, entitled "INTRODUCER NEEDLE WITH NOTCHES FOR IMPROVED FLASHBACK," which is a continuation-in-part of U.S. patent application Ser. No. 15/946,593, filed Apr. 5, 2018, entitled "INTRODUCER NEEDLE WITH NOTCHES FOR IMPROVED FLASHBACK," which are hereby incorporated by reference in their entirety.

BACKGROUND OF THE INVENTION

Intravenous (IV) catheters are commonly used for a variety of infusion therapies. For example, IV catheters may be used for infusing normal priming fluid, various medicaments, or total parenteral nutrition into a patient. IV catheters may also be used for withdrawing blood from the patient.

A common type of IV catheter is an over-the-needle peripheral IV catheter. As its name implies, the over-the-needle peripheral IV catheter may be mounted over an introducer needle having a sharp distal tip. The sharp distal tip may be used to pierce skin and a vasculature of the patient. Insertion of the IV catheter into the vasculature may follow the piercing of the vasculature by the introducer needle. The introducer needle and the IV catheter are generally inserted at a shallow angle through the skin into the vasculature of the patient with a bevel of the introducer needle facing away from the skin of the patient.

In order to verify proper placement of the introducer needle and/or the IV catheter in the vasculature, a clinician generally confirms that there is flashback of blood, which may be visible to the clinician. In some instances, the introducer needle may include a single notch, and in response to the distal tip of the introducer needle being positioned within the vasculature, blood may flow proximally through a needle lumen, exit the needle lumen through the notch, and then travel proximally between an outer surface of the introducer needle and an inner surface of another device (e.g., the IV catheter). Accordingly, where the other device is at least partially transparent, the clinician may visualize a small amount of blood "flashback" and thereby confirm placement of the catheter within the vasculature. Presence of a vasculature entrance indicator, such as flashback, may facilitate successful placement of IV catheters. Once placement of the introducer needle within the vasculature has been confirmed, the clinician may temporarily occlude flow in the vasculature and withdraw the introducer needle, leaving the catheter in place for future blood withdrawal and/or fluid infusion.

In some markets, priming of the IV catheter is common practice. In order to prime the IV catheter, the clinician may fill the IV catheter with saline or another priming fluid to reduce or eliminate any air pockets disposed within the IV catheter. The saline may also fill a portion of a needle lumen proximate the notch, as well as distal to the notch, all the way to the distal tip of the introducer needle. Thus, when the distal tip of the introducer needle enters the vasculature, flashback may be slowed due to diffusion. Flashback may also be difficult to visualize due to mixing of flashback with the saline.

Furthermore, many integrated IV catheter systems having an integrated extension tube do not include a flash chamber, which may be vented. Examples of integrated IV catheter systems may include, for example, the BD NEXIVA™ Closed IV Catheter System, the BD NEXIVA™ DIFFUSICS™ Closed IV Catheter System, or the Becton Dickinson PEGASUS™ Safety Closed IV Catheter System. Thus, after the priming of the IV catheter, the IV catheter system may no longer be vented, and when the distal tip of the introducer needle enters the vasculature, blood may only slowly diffuse into the introducer needle. Also, transfixing of the vasculature may not be observed since the proximal diffusion of the blood may continue even when the distal tip is no longer properly placed within the vasculature.

Moreover, sometimes the clinician may not prime the integrated IV catheter system and may instead wait for flashback to flow through the integrated IV catheter system to purge any air from the integrated IV catheter system. For example, the clinician may wait for blood within the integrated IV catheter system to flow proximally through the introducer needle, out the notch, and through the IV catheter, a catheter adapter, and the integrated extension tube to a luer adapter, where air may exit the integrated IV catheter system. Such a process may be time consuming.

It is to be understood that both the foregoing general description and the following detailed description are exemplary and explanatory and are not restrictive of the invention, as claimed.

BRIEF SUMMARY OF THE INVENTION

The present disclosure relates generally to an introducer needle having a first notch and a second notch, and related devices, systems, and methods. In some embodiments, the introducer needle may include a proximal end, a distal tip, and a needle lumen extending between the proximal end and the distal tip. In some embodiments, the introducer needle may include a wall, which may define the needle lumen. In some embodiments, the first notch may be formed through the wall, and the second notch may be formed through the wall. In some embodiments, the second notch may be proximal to the first notch.

In some embodiments, a catheter system may include a catheter adapter, which may include a distal end, a proximal end, and a lumen extending between the distal end and the proximal end. In some embodiments, the catheter system may include a catheter, which may include an IV catheter, such as a peripheral IV catheter, for example. In some embodiments, the catheter may extend distally from the distal end of the catheter adapter. In some embodiments, the catheter system may include the introducer needle, which may extend through the catheter and beyond the distal end of the catheter when the introducer needle is in an insertion position for insertion into vasculature of a patient.

In some embodiments, the first notch of the introducer needle may be disposed within the catheter when the introducer needle is in the insertion position. In some embodiments, at least a portion of the catheter may be transparent or translucent. In some embodiments, where the proximal end of the introducer needle is vented such that air and/or fluid may travel proximally through the introducer needle, presence of the first and second notches may facilitate pressure-driven blood flow into the catheter for improved flashback and detection of transfixing. In some embodiments, the first and second notches may improve first needle stick success by improving the quality of flashback.

In further detail, in some embodiments, the catheter system may include a first fluid pathway, which may extend from the first notch to the second notch between an outer surface of the introducer needle and an inner surface of a wall of the catheter, and a second fluid pathway, which may extend from the first notch to the second notch within the needle lumen. During flashback, blood may flow through the first fluid pathway and/or the second fluid pathway. In some embodiments, the first fluid pathway may provide pressure-driven flashback, even after the catheter system is primed. In some embodiments, flashback may be faster through the first fluid pathway than the second fluid pathway. In some embodiments, flashback through the first fluid pathway may be visible due to the transparency of the catheter.

In some embodiments, the first fluid pathway may have a larger volume than the second fluid pathway, which may facilitate faster flashback through the first fluid pathway than the second fluid pathway. In some embodiments, a cross-section taken through the catheter system perpendicular to a central axis of the catheter system and between the first notch and the second notch may include a needle lumen area and another area between the outer surface of the introducer needle and the inner surface of the wall of the catheter. In some embodiments, the other area may be greater than the needle lumen area. In some embodiments, the other area may be greater than the needle lumen area in each cross-section taken through the catheter system perpendicular to the central axis along an entire length between the first notch and the second notch.

In some embodiments, the catheter system may include a flash chamber, which may facilitate flashback. In some embodiments, the flash chamber may be in fluid communication with the needle lumen. In some embodiments, the flash chamber may include a gas permeable vent. In some embodiments, the gas permeable vent of the flash chamber may provide the venting that allows air and/or fluid to travel proximally through the introducer needle. In some embodiments, the flash chamber may be disposed proximal to the proximal end of the introducer needle. In some embodiments, the gas permeable vent may provide at least some resistance to air flow.

In some embodiments, the catheter may be primed prior to insertion of the catheter and introducer needle into the vasculature of the patient. In some embodiments, the catheter may be primed when the introducer needle is in the insertion position. In some embodiments, in order to prime the catheter, the clinician may fill the catheter with a priming fluid, such as, for example, saline, to reduce or eliminate any air pockets disposed within the catheter. In some embodiments, the priming fluid may be disposed in a first portion of a needle lumen proximate the first notch and including the distal tip of the introducer needle. Additionally, in some embodiments, the priming fluid may be disposed in a second portion of the needle lumen proximate the second notch. In some embodiments, when the gas permeable vent provides the resistance, the priming fluid in the first portion may be separated from the priming fluid in the second portion, and air may be disposed between the first portion and the second portion in the needle lumen.

In some embodiments, in response to the distal tip of the introducer needle entering the vasculature, blood pressure will drive the flashback into the needle. Additionally, in some embodiments, at least some of the flashback may then be driven out of the introducer needle at the first notch and into the catheter. Furthermore, in some embodiments, in response to the distal tip of the introducer needle entering the vasculature, the priming fluid outside the introducer needle and within the catheter tube between the first notch and the second notch may be driven into the introducer needle through the second notch and may eventually reach the flash chamber. In some embodiments, in response to the distal tip of the introducer needle entering the vasculature, blood may flow proximally through the needle as well. In some embodiments, the pressure-driven blood flow through the first fluid pathway, which may initially be filled with the priming fluid, may be faster than diffusion.

In some embodiments, the flash chamber may include a large, non-restrictive volume, which may facilitate the pressure-driven flow of the priming fluid and/or blood towards or into the flash chamber. In some embodiments, a volume of the flash chamber may be large enough to hold the priming fluid disposed outside the introducer needle and within the catheter between the first notch and the second notch and/or the priming fluid that may travel into the flash chamber during priming of the catheter. Additionally, in some embodiments, the volume of the flash chamber may be large enough to hold blood when the distal tip of the introducer needle is disposed within the vasculature.

In some embodiments, a portion of the wall of the introducer needle between the first notch and the second notch may be pinched or crimped such that fluid, such as blood, is prevented from flowing in the needle lumen between the first notch and the second notch. In some embodiments, the crimped portion of the wall may facilitate rapid flashback through the first fluid pathway.

In some embodiments, the second notch may be disposed within the catheter when the needle is in the insertion position. In some embodiments, the second notch may be disposed within the lumen of the catheter adapter when the needle is in the insertion position. In some embodiments, a distance between the first notch and the second notch may be greater than a length of the catheter, which may facilitate visibility of transfixing.

In some embodiments, the catheter system may include a needle hub, which may be coupled to the catheter adapter when the introducer needle is in the insertion position. In some embodiments, a proximal end of the introducer needle may be secured within the needle hub. In some embodiments, the flash chamber may be disposed within the needle hub.

In some embodiments, the catheter system may include a blood control septum, which may be disposed within the lumen of the catheter adapter. In some embodiments, the septum may divide the lumen of the catheter adapter into a proximal chamber and a distal chamber. In some embodiments, the second notch may be disposed distal to the septum when the introducer needle is in the insertion position.

In some embodiments, the catheter adapter may include a gas permeable vent, which may be selectively opened and/or closed. In some embodiments, the gas permeable vent of the catheter adapter may be disposed distal to the septum such that air in the distal chamber may freely flow out of the gas permeable vent when the vent is opened. In some embodiments, the gas permeable vent of the catheter adapter may be opened during priming of the catheter, which may prevent the priming fluid from being disposed in the first portion of the needle proximate the first notch and/or the second portion of the needle proximate the second notch, as the gas permeable vent of the catheter adapter may provide a path of low resistance for the priming fluid.

In some embodiments, the catheter system may include a seal, which may be secured within the lumen of the catheter adapter. In these and other embodiments, the portion of the wall of the introducer needle between the first notch and the second notch may be pinched or crimped such that fluid is prevented from flowing in the needle lumen between the first notch and the second notch. In some embodiments, the introducer needle may be rotatable from a priming position to the insertion position and/or from the insertion position to the priming position. In some embodiments, the introducer needle may be disposed in the priming position during priming of the catheter and may be disposed in the insertion position during insertion into the vasculature.

In some embodiments, when the introducer needle is in the priming position, the seal may cover and seal the second notch, which may prevent fluid from flowing through the second notch. In some embodiments, when the introducer needle is in the insertion position, the seal may not cover or seal the second notch and fluid may flow through the second notch. In some embodiments, in response to the second notch being uncovered or unsealed, rapid flashback may occur with blood flowing into the needle lumen via the second notch. In some embodiments, the seal may include a septum or flapper.

In some embodiments, the introducer needle may be rotatable between the priming position and the insertion position about the central axis of the catheter system, which may extend through the needle lumen. In some embodiments, the introducer needle may be rotated by twisting the needle hub. In some embodiments, the introducer needle may be rotated in a first direction and/or a second direction opposite the first direction. In some embodiments, the second notch may be aligned with the seal when the introducer needle is in the priming position and the insertion position. In these and other embodiments, the introducer needle may extend a same distance from the distal tip of the catheter when the introducer needle is in the priming position as when the introducer needle is in the insertion position.

In some embodiments, the catheter system may include a plug constructed of a dissolvable material. In some embodiments, the plug may be disposed on top of the second notch to seal the second notch during priming of the catheter system.

In some embodiments, the catheter adapter of the catheter system may include the distal end, the proximal end, the lumen extending between the distal end and the proximal end, and a side port. In some embodiments, the side port may be disposed between the distal end of the catheter adapter and the proximal end of the catheter adapter and may be in fluid communication with the lumen of the catheter adapter. In some embodiments, an extension tube may be integrated within the side port. In some embodiments, the catheter may extend distally from the distal end of the catheter adapter.

In some embodiments, the introducer needle may include the wall defining the needle lumen, the first notch formed through the wall, and the second notch formed through the wall. In some embodiments, the second notch may be proximal to the first notch. In some embodiments, the introducer needle may extend through the catheter and beyond the distal end of the catheter when the introducer needle is in the insertion position for insertion into the patient.

In some embodiments, the catheter system may include a seal element. In some embodiments, the seal element may block a fluid pathway that extends from the extension tube through the catheter. In some embodiments, the seal element may be disposed proximal to the second notch and distal to the side port. In some embodiments, the seal element may prevent the priming fluid from travelling distal to the seal element between the outer surface of the introducer needle and the inner surface of the catheter. In some embodiments, the seal element may be disposed within the catheter between the outer surface of the introducer needle and an inner surface of the catheter. In some embodiments, the seal element may be disposed within the catheter adapter between the outer surface of the introducer needle and an inner surface of the catheter adapter.

In some embodiments, a portion of an outer surface of the introducer needle may include a groove. In some embodiments, the portion of the outer surface of the introducer needle may be disposed within the septum. In some embodiments, the groove may be configured to allow air to pass through the septum.

In some embodiments, the needle hub may include the flash chamber, which may be in fluid communication with the needle lumen. In some embodiments, the needle hub may include a gas permeable vent proximate the flash chamber. In some embodiments, the catheter adapter may include a gas permeable vent proximal to the septum.

In some embodiments, the needle hub may include another extension tube. In some embodiments, a distal end of the other extension tube may be in fluid communication with the flash chamber. In some embodiments, a proximal end of the other extension tube may be coupled to a holder configured to receive an evacuated blood collection tube. In some embodiments, the catheter system may include a needle safety, which may be disposed between the needle hub and the catheter adapter.

In some embodiments, a method may include coupling a device containing priming fluid to an adapter of the catheter system. In some embodiments, the adapter may include a Y-adapter or another suitable adapter. In some embodiments, the adapter may be coupled to the proximal end of the extension tube. In some embodiments, the method may include priming the catheter system with by activating the device containing priming fluid such that the priming fluid flows distally through the catheter system to the seal element and stops at the seal element. In some embodiments, after priming the catheter system with the device containing priming fluid such that the priming fluid flows distally through the catheter system to the seal element and stops at the seal element, the method may include inserting the catheter into vasculature.

In some embodiments, in response to inserting the catheter into the vasculature, blood may flow proximally into the needle lumen, then out of the needle lumen through the first notch into a space between an outer surface of the introducer needle and an inner surface of the catheter, and then into the needle lumen through the second notch. In some embodiments, after the blood flows into the needle lumen through the second notch, the blood may flow into the flash chamber and/or through the other extension tube. In some embodiments, after inserting the catheter into the vasculature, blood may be collected using the catheter system.

In some embodiments, after inserting the catheter into the vasculature and/or collecting blood, the method may include withdrawing the introducer needle in a proximal direction. In some embodiments, in response to withdrawing the introducer needle in the proximal direction, a seal formed by the seal element may be broken such that the priming fluid joins the blood disposed within the catheter distal to the seal. In some embodiments, in response to the seal being broken, the catheter may remain in place within the vasculature for use in future infusions and/or blood draw.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3A is a top view of an example needle assembly, according to some embodiments;

FIG. 3B is a partial cutaway view of the needle assembly of FIG. 3A, according to some embodiments;

FIG. 5B is an enlarged cross-sectional view of a distal end of the catheter system of FIG. 5A, according to some embodiments;

FIG. 5C is an enlarged cross-sectional view of a portion of the catheter system of FIG. 5A, according to some embodiments;

DETAILED DESCRIPTION OF THE INVENTION

Figure 1:
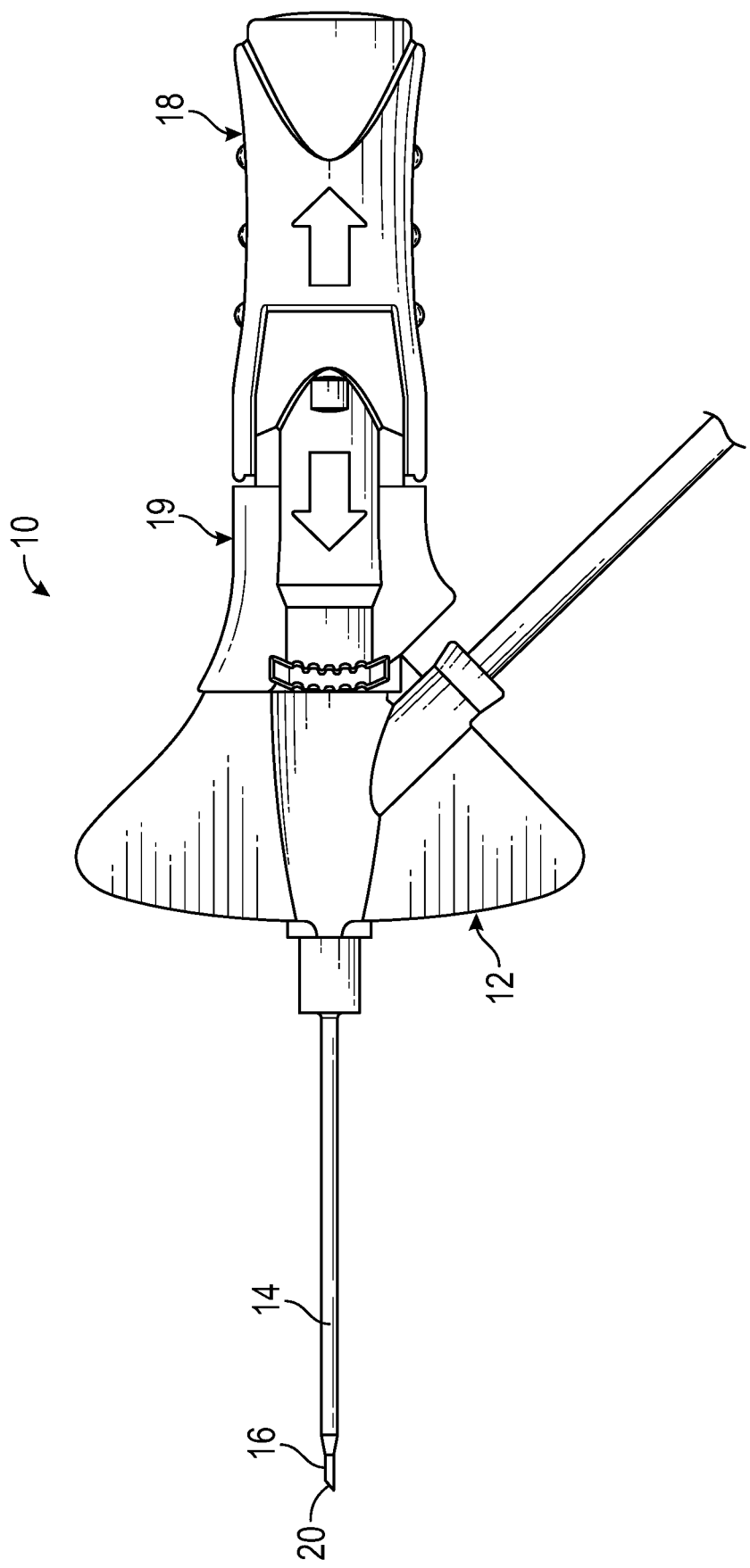
FIG. 1 is a top view of an example catheter system, illustrating the catheter system in an insertion position, according to some embodiments.

The present disclosure relates generally to an introducer needle having a first notch and a second notch, and related devices, systems, and methods. Referring now to FIG. 1, in some embodiments, a catheter system 10 may include a catheter adapter 12, which may include a distal end, a proximal end, and a lumen extending between the distal end and the proximal end. In some embodiments, the catheter system 10 may include a catheter 14, which may include an IV catheter, such as a peripheral IV catheter, for example. In some embodiments, the catheter 14 may extend distally from the distal end of the catheter adapter 12. In some embodiments, the catheter system 10 may include the introducer needle 16, which may extend through the catheter 14 and beyond the distal end of the catheter 14 when the introducer needle 16 is in an insertion position for insertion into vasculature of a patient.

In some embodiments, the catheter system 10 may include a needle hub 18, which may be coupled to the catheter adapter 12 when the introducer needle 16 is in the insertion position. In some embodiments, a proximal end of the introducer needle 16 may be secured within the needle hub 18. In some embodiments, the catheter system 10 may include a needle shield 19. In some embodiments, the catheter system 10 may be integrated or non-integrated. In some embodiments, the catheter system 10 may include the needle shield 19 or any other type of suitable needle safety mechanism.

Figure 2A:
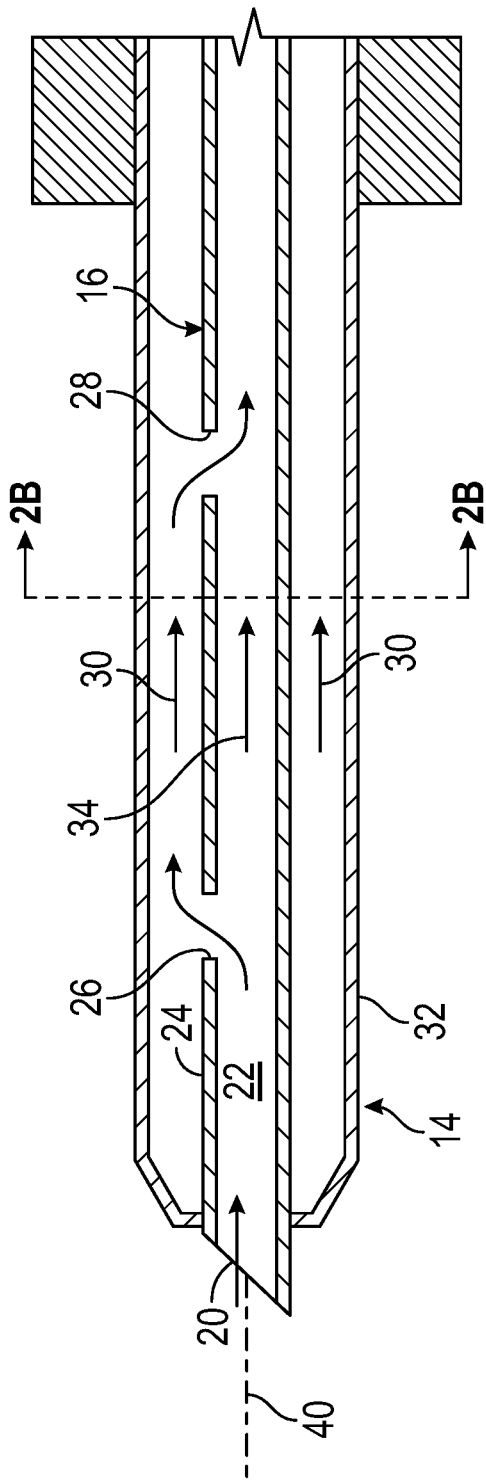
FIG. 2A is a cross-sectional view of an example introducer needle disposed within a an example catheter, illustrating the introducer needle in the insertion position, according to some embodiments.

Referring now to FIG. 2A, in some embodiments, the introducer needle 16 may include a proximal end, a distal tip 20, and a needle lumen 22 extending between the proximal end and the distal tip 20. In some embodiments, the introducer needle 16 may include a wall 24, which may define the needle lumen 22. In some embodiments, the first notch 26 may be formed through the wall 24, and the second notch 28 may be formed through the wall 24. In some embodiments, the second notch 28 may be proximal to the first notch 26. In some embodiments, the wall 24 may include more than two notches.

In some embodiments, the first notch 26 of the introducer needle 16 may be disposed within the catheter 14 when the introducer needle 16 is in the insertion position. In some embodiments, at least a portion of the catheter 14 may be transparent or translucent. In some embodiments, presence of the second notch 28 may facilitate pressure-driven blood flow into the catheter 14 for improved flashback and detection of transfixing. In some embodiments, the second notch 28 may improve first needle stick success by improving the quality of flashback.

In further detail, in some embodiments, the catheter system 10 may include a first fluid pathway 30, which may extend from the first notch 26 to the second notch 28 between an outer surface of the introducer needle 16 and an inner surface of a wall 32 forming the catheter 14, and a second fluid pathway 34, which may extend from the first notch 26 to the second notch 28 within the needle lumen 22. In some embodiments, during flashback, blood may flow through the first fluid pathway 30 and/or the second fluid pathway 34. In some embodiments, the first fluid pathway 30 may provide pressure-driven flashback, even after the catheter system 10 is primed. In some embodiments, flashback or proximal blood travel may be faster through the first fluid pathway 30 than the second fluid pathway 34. In some embodiments, flashback through the first fluid pathway 30 may be visible due to the transparency or translucency of the catheter 14.

In some embodiments, the second notch 28 may be disposed within the catheter 14 when the introducer needle 16 is in the insertion position. In some embodiments, the second notch 28 may be disposed within the lumen of the catheter adapter (as illustrated, for example, in FIGS. 4A-4B) when the introducer needle 16 is in the insertion position. In some embodiments, a distance between the first notch 26 and the second notch 28 may be greater than a length of the catheter 14, which may facilitate visibility of transfixing.

Figure 2B:
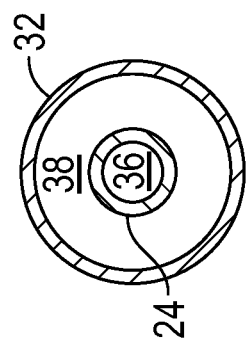
FIG. 2B is a cross-sectional view along line 2B-2B of FIG. 2A, according to some embodiments.

In some embodiments, the first fluid pathway 30 may have a larger volume than the second fluid pathway 34, which may facilitate faster flashback or proximal blood travel through the first fluid pathway 30 than the second fluid pathway 34. Referring now to FIG. 2B, in some embodiments, a cross-section taken through the catheter system 10 perpendicular to a central axis 40 of the catheter system 10 and between the first notch 26 and the second notch 28 may include a needle lumen area 36 and another area 38 between the outer surface of the introducer needle 16 and the inner surface of the wall 32 of the catheter 14. In some embodiments, the other area 38 may be greater than the needle lumen area 36. In some embodiments, the other area 38 may be greater than the needle lumen area 36 in each cross-section taken through the catheter system 10 perpendicular to the central axis 40 along an entire length between the first notch 26 and the second notch 28.

Figure 2C:
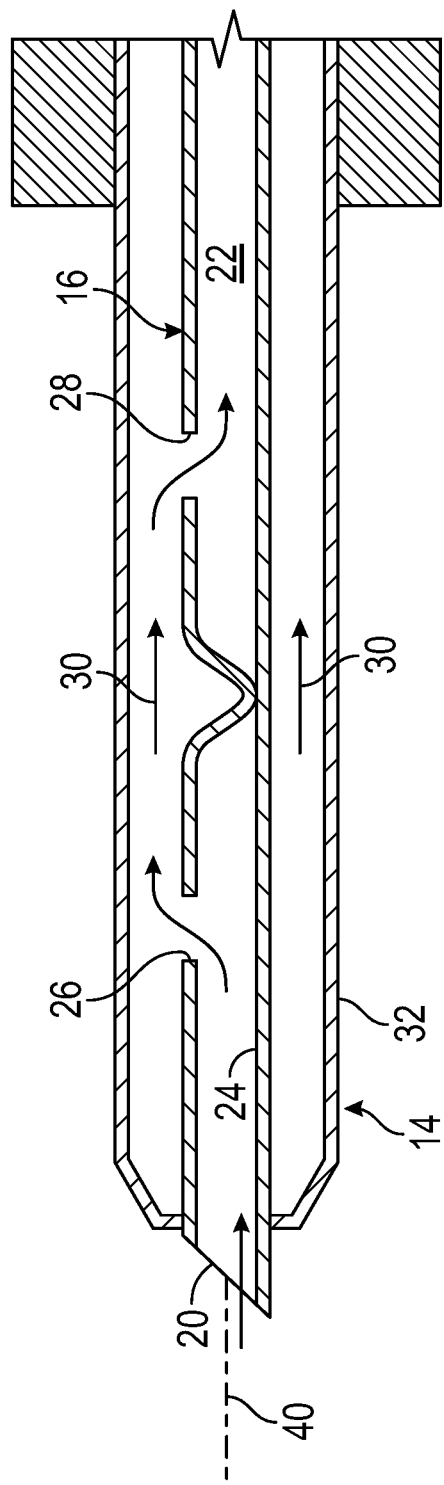
FIG. 2C is a cross-sectional view of the introducer needle of FIG. 2A having an example crimp feature and disposed within the catheter, illustrating the introducer needle in the insertion position, according to some embodiments.

Referring now to FIG. 2C, in some embodiments, a portion of the wall 24 of the introducer needle 16 between the first notch 26 and the second notch 28 may be pinched or crimped such that fluid, such as blood, is prevented from flowing in the needle lumen 22 between the first notch 26 and the second notch 38. In some embodiments, the crimped portion 42 of the wall 24 may facilitate rapid flashback through the first fluid pathway 30.

Figure 2D:
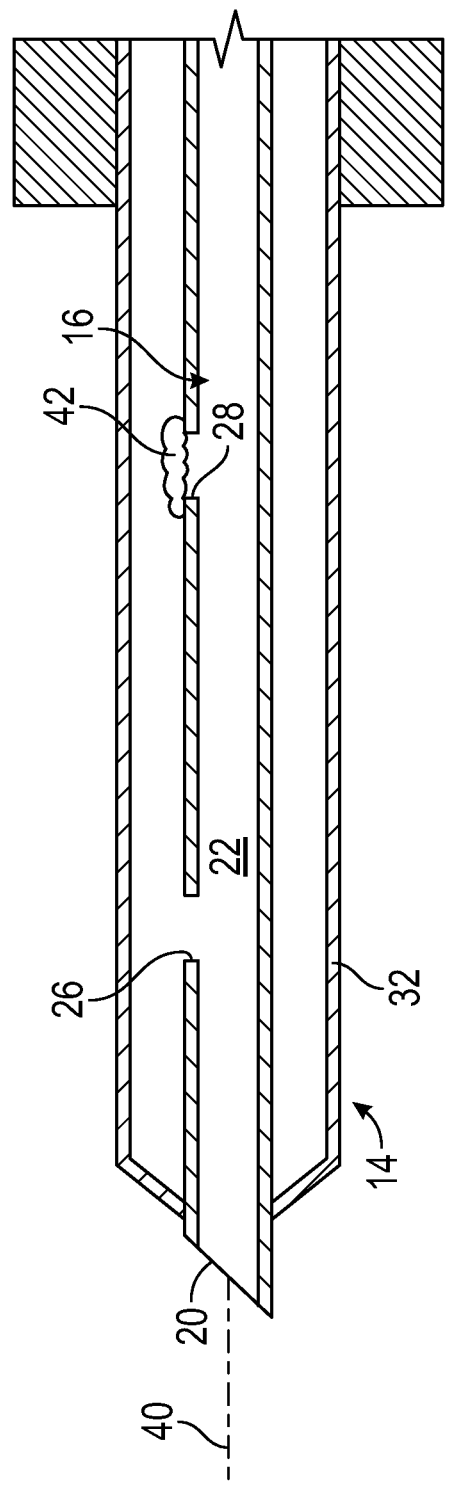
FIG. 2D is a cross-sectional view of the introducer needle of FIG. 2A disposed within the catheter, illustrating the introducer needle in the insertion position and an example plug constructed of a dissolvable material, according to some embodiments.

Referring now to FIG. 2D, in some embodiments, a plug 42, which may be constructed of a dissolvable material, may seal the second notch 28 during priming of the catheter 14. In some embodiments, the plug 42 may be dissolved when the catheter system 10 is introduced into the vasculature of the patient.

Figure 2E:
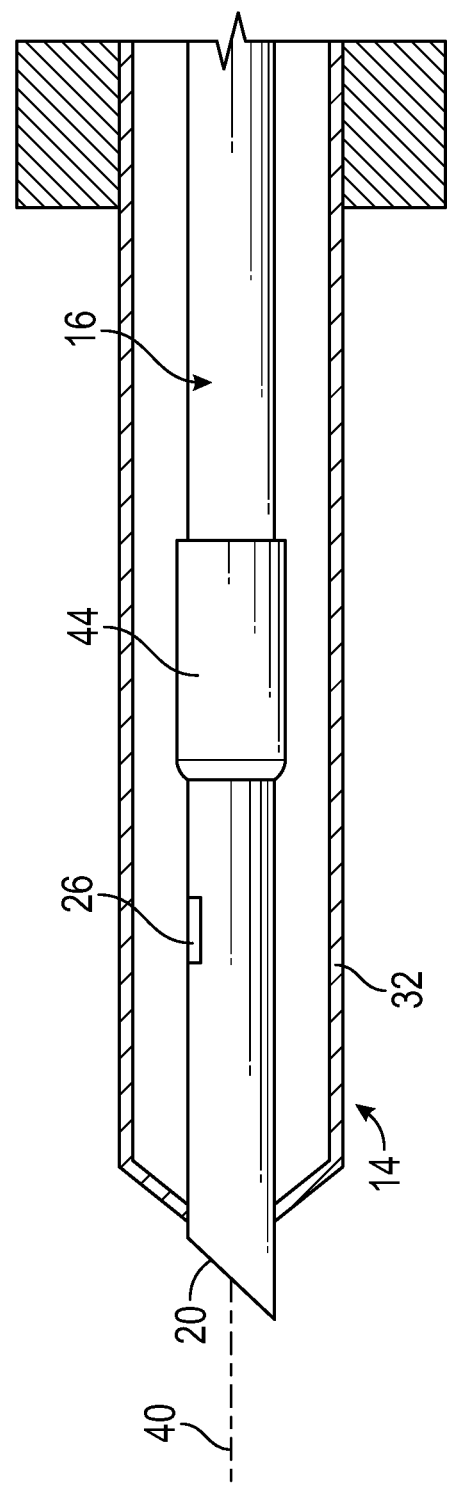
FIG. 2E is a partial cutaway of the introducer needle of FIG. 2A disposed within the catheter, illustrating the introducer needle in the insertion position and a sleeve element constructed of a dissolvable material, according to some embodiments.

Referring now to FIG. 2E, in some embodiments, a sleeve 44, which may be constructed of a dissolvable material, may seal the second notch 28 during priming of the catheter 14. In some embodiments, the sleeve 44 may be dissolved when the catheter system 10 is introduced into the vasculature of the patient.

Referring now to FIGS. 3A-3B, in some embodiments, the catheter system 10 may include a flash chamber 46, which may facilitate flashback. In some embodiments, the flash chamber 46 may be in fluid communication with the needle lumen 22. In some embodiments, the flash chamber 46 may include a gas permeable vent 48. In some embodiments, the flash chamber 46 may be disposed proximal to the proximal end 49 of the introducer needle 16. In some embodiments, the gas permeable vent 48 may provide at least some resistance to air flow. In some embodiments, the flash chamber 46 may be disposed within the needle hub 18, as illustrated, for example, in FIG. 3B. FIGS. 3A-3B illustrate a needle assembly with the needle shield 19 removed, according to some embodiments.

In some embodiments, the catheter 14 may be primed prior to insertion of the catheter 14 and the introducer needle 16 into the vasculature of the patient. In some embodiments, the catheter 14 may be primed when the introducer needle 16 is in the insertion position. In some embodiments, in order to prime the catheter 14, the clinician may fill the catheter 14 with a priming fluid, such as, for example, saline, to reduce or eliminate any air pockets disposed within the catheter. In some embodiments, the priming fluid may be disposed in a first portion of a needle lumen proximate the first notch 26 and including the distal tip 20 of the introducer needle 16. Additionally, in some embodiments, the priming fluid may be disposed in a second portion of the needle lumen 22 proximate the second notch 28. In some embodiments, when the gas permeable vent 48 provides the resistance, the priming fluid in the first portion may be separated from the priming fluid in the second portion, and air may be disposed between the first portion and the second portion in the needle lumen 22.

In some embodiments, in response to the distal tip 20 of the introducer needle 16 entering the vasculature, blood pressure will drive the flashback into the introducer needle 16. Additionally, in some embodiments, at least some of the flashback may then be driven out of the introducer needle 16 at the first notch 26 and into the catheter 14. Furthermore, in some embodiments, in response to the distal tip 20 of the introducer needle 16 entering the vasculature, the priming fluid outside the introducer needle 16 and within the catheter 14 between the first notch 26 and the second notch 28 may be driven into the introducer needle 16 through the second notch 28 and may eventually reach the flash chamber 46. In some embodiments, in response to the distal tip 20 of the introducer needle 16 entering the vasculature, blood may flow proximally through the introducer needle 16 as well. In some embodiments, the pressure-driven blood flow through the first fluid pathway 30, which may initially be filled with the priming fluid, may be faster than diffusion.

In some embodiments, the flash chamber 46 may include a large, non-restrictive volume, which may facilitate the pressure-driven flow of the priming fluid and/or blood towards or into the flash chamber 46. In some embodiments, a volume of the flash chamber 46 may be large enough to hold the priming fluid disposed outside the introducer needle 16 and within the catheter 14 between the first notch 26 and the second notch 28 and/or the priming fluid that may travel into the flash chamber 46 during priming of the catheter 14. Additionally, in some embodiments, the volume of the flash chamber 46 may be large enough to hold blood when the distal tip 20 of the introducer needle 16 is disposed within the vasculature.

Figure 4A:
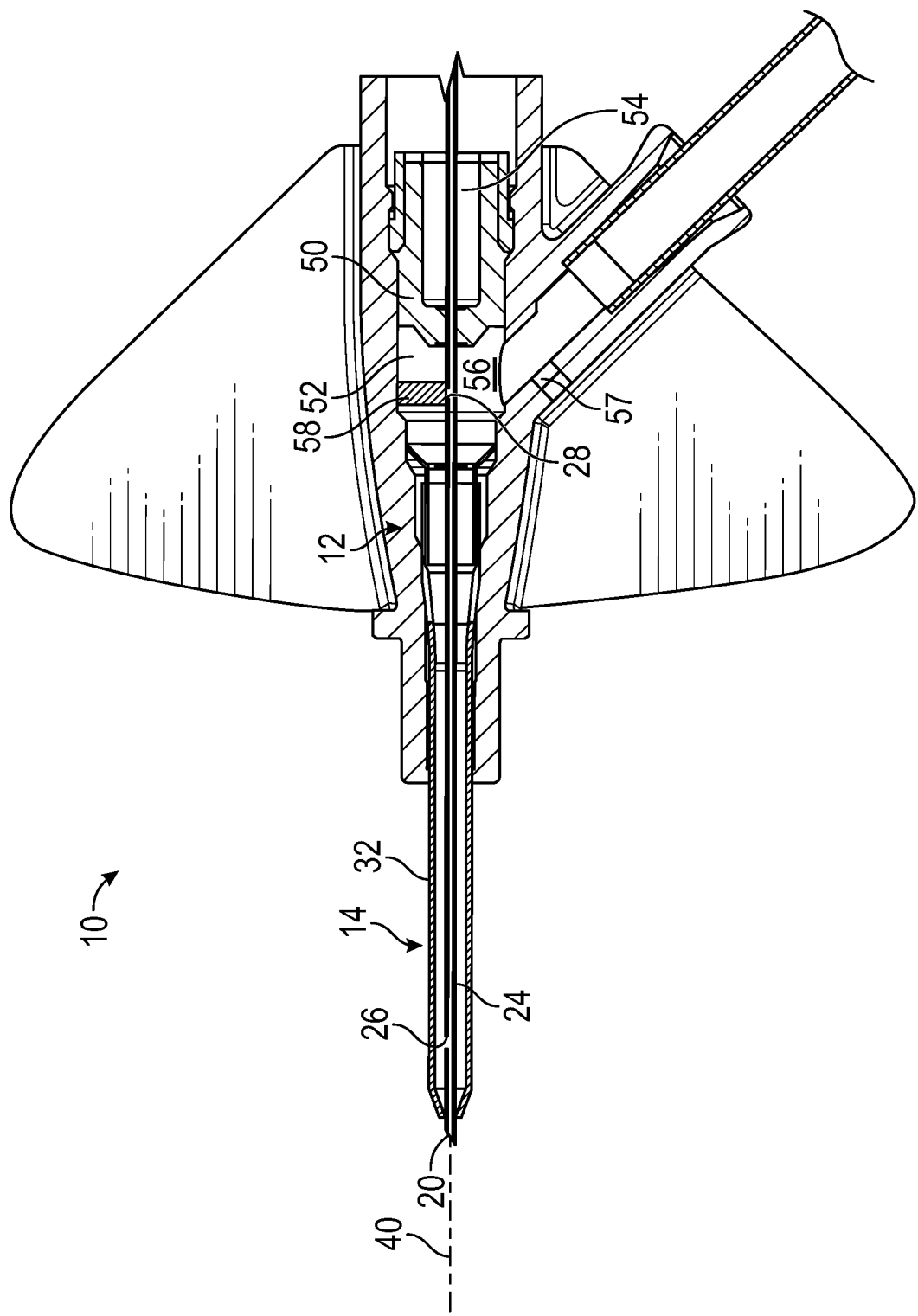
FIG. 4A is a cross-sectional view of the catheter system of FIG. 1A, illustrating the catheter system in the insertion position and an example seal covering an example second notch, according to some embodiments.
Figure 4B:
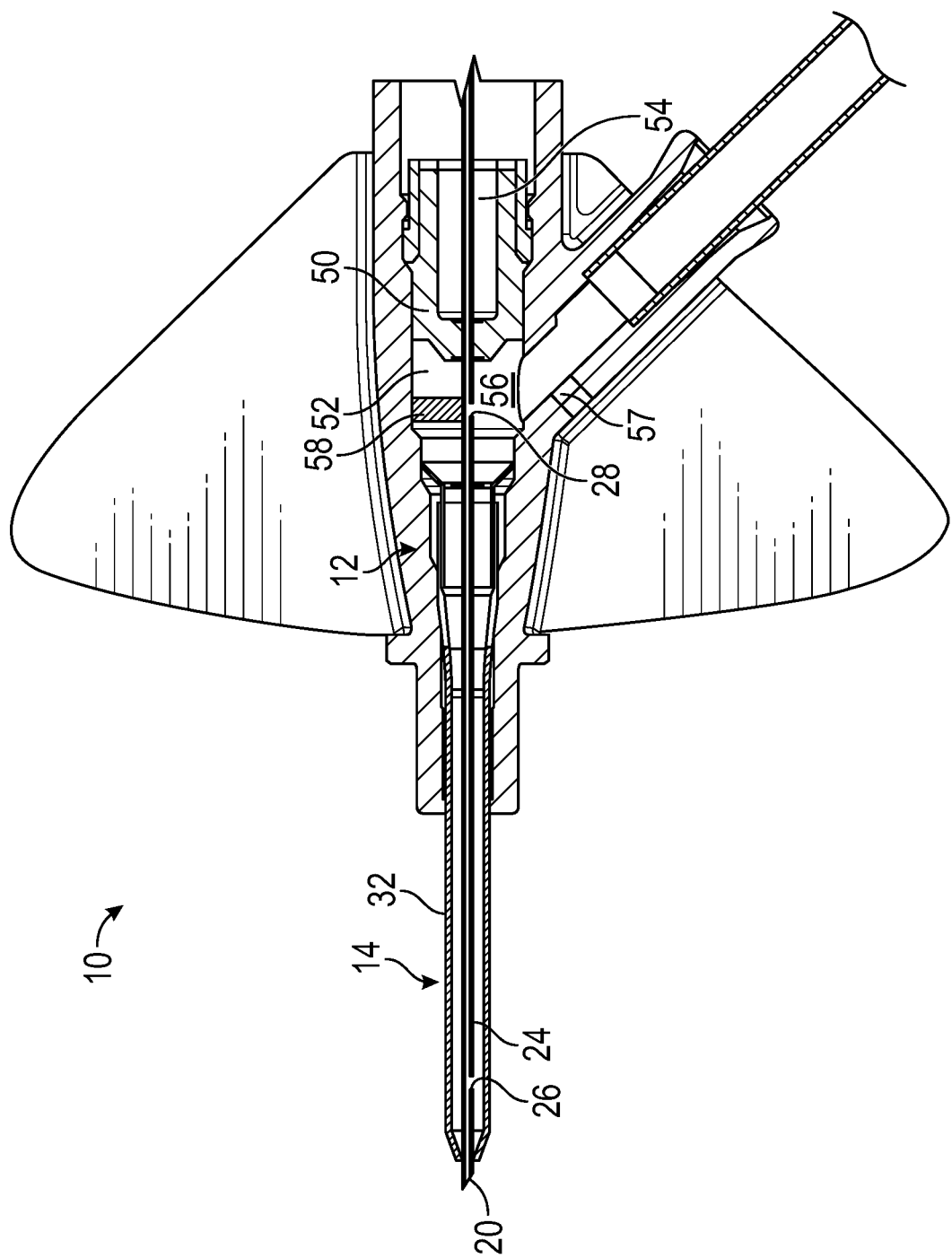
FIG. 4B is a cross-sectional view of the catheter system of FIG. 1A, illustrating the seal removed from the second notch, according to some embodiments.

Referring now to FIGS. 4A-4B, in some embodiments, the catheter system 10 may include a blood control septum 50, which may be disposed within the lumen 52 of the catheter adapter 12. In some embodiments, the septum 50 may divide the lumen 52 of the catheter adapter 12 into a proximal chamber 54 and a distal chamber 56. In some embodiments, the second notch 28 may be disposed distal to the septum 50 when the introducer needle 16 is in the insertion position.

In some embodiments, the catheter adapter 12 may include a gas permeable vent 57, which may be selectively opened and/or closed. In some embodiments, the gas permeable vent 57, which may be disposed through a wall of the catheter adapter 12, may be disposed distal to the septum 50 such that air in the distal chamber 56 may freely flow out of the gas permeable vent 57 when the gas permeable vent 57 is opened. In some embodiments, the gas permeable vent 57 of the catheter adapter 12 may be opened during priming of the catheter 14, which may prevent the priming fluid from being disposed in the first portion of the introducer needle 16 proximate the first notch 26 and/or the second portion 28 of the introducer needle 16 proximate the second notch 28.

In some embodiments, the catheter system 10 may include a seal 58, which may be secured within the lumen 52 of the catheter adapter 12. In these and other embodiments, the portion of the wall of the introducer needle 16 between the first notch 26 and the second notch 28 may be pinched or crimped such that fluid is prevented from flowing in the needle lumen 22 between the first notch 26 and the second notch 28. In some embodiments, the introducer needle 22 may be rotatable from a priming position to the insertion position and/or from the insertion position to the priming position. FIG. 4A illustrates the introducer needle 22 in the insertion position, according to some embodiments, and FIG. 4B illustrates the introducer needle 22 in the priming position, according to some embodiments. In some embodiments, the introducer needle 16 may be disposed in the priming position during priming of the catheter and may be disposed in the insertion position during insertion into the vasculature. In some embodiments, the catheter system 10 may not include the seal 58 and/or the priming and insertions positions may be the same.

In some embodiments, when the introducer needle 16 is in the priming position, the seal 58 may cover or seal the second notch, which may prevent fluid from flowing through the second notch 28. In some embodiments, when the introducer needle 16 is in the insertion position, the seal 58 may not cover or seal the second notch 28 and fluid may flow through the second notch 28. In some embodiments, in response to the second notch 28 being uncovered or unsealed, rapid flashback may occur with blood flowing into the needle lumen 22 via the second notch 28. In some embodiments, the seal 58 may include a septum or flapper.

In some embodiments, the introducer needle 16 may be rotatable between the priming position and the insertion position about the central axis 40 of the catheter system 10, which may extend through the needle lumen 22. In some embodiments, the introducer needle 16 may be rotated by twisting the needle hub 18. In some embodiments, the introducer needle 16 may be rotated in a first direction and/or a second direction opposite the first direction. In some embodiments, the second notch 28 may be aligned with the seal when the introducer needle is in the priming position and the insertion position, as illustrated in FIGS. 4A-4B, for example. In these and other embodiments, the introducer needle 16 may extend a same distance from the distal tip of the catheter 14 when the introducer needle 16 is in the priming position as when the introducer needle 16 is in the insertion position.

Referring now to FIGS. 5A-5F, a catheter system 60 is illustrated, according to some embodiments. In some embodiments, the catheter system 60 may be similar or identical to the catheter system 10 discussed with respect to FIGS. 1-4A in terms of one or more included features and/or operation. In some embodiments, the catheter system 60 may facilitate priming of the catheter system 60 and reduction of air within the catheter system 60 prior to insertion into the vasculature of the patient. In these and other embodiments, the catheter system 60 may also allow the clinician to see both primary flashback within the catheter 14 and secondary flashback within the flash chamber 46 with blood that is not diluted with priming fluid. In some embodiments, the catheter system 60 facilitates priming of a portion of the catheter system 60 prior to insertion of the catheter system 60 into the vasculature of the patient while still allowing efficient blood flashback for vein confirmation.

In some embodiments, the catheter system 60 may include the catheter adapter 12, which may include a distal end 62, a proximal end 64, the lumen 52 extending between the distal end 62 and the proximal end 64, and a side port 68. In some embodiments, the side port 68 may be disposed between the distal end 62 of the catheter adapter 12 and the proximal end 64 of the catheter adapter 12 and may be in fluid communication with the lumen 52 of the catheter adapter 12. In some embodiments, an extension tube 70 may be integrated within the side port 68.

In some embodiments, the catheter 14 may extend distally from the distal end 62 of the catheter adapter 12. In some embodiments, the catheter 14 may include a peripheral IV catheter, a midline IV catheter, or a peripherally inserted central catheter. In some embodiments, the introducer needle 16 may include the wall 24 defining the needle lumen 22, the first notch 26 formed through the wall 24, and the second notch 28 formed through the wall 24. In some embodiments, the second notch 28 may be proximal to the first notch 26. In some embodiments, the introducer needle 16 may extend through the catheter 14 and beyond the distal end of the catheter 14 when the introducer needle 16 is in the insertion position for insertion into the patient. In some embodiments, the first notch 26 and/or the second notch 28 may be disposed within the catheter 14 when the introducer needle 16 is in the insertion position.

In some embodiments, the introducer needle 16 may include a block 71 disposed between the first notch 26 and the second notch 28. For example, a portion of the wall of the introducer needle between the first notch 26 and the second notch 28 may be pinched or crimped such that fluid, such as blood, may be prevented from flowing in the needle lumen 22 between the first notch 26 and the second notch 28. In some embodiments, the block 71 may facilitate rapid flashback through the first fluid pathway 30 (see, for example, FIG. 2C).

In some embodiments, the catheter system 60 may include a seal element 72. In some embodiments, the seal element 72 may block a fluid pathway that extends through the extension tube 70 through the catheter 14. In some embodiments, the seal element 72 may be disposed proximal to the second notch 28 and distal to the side port 68 or a junction between the side port 68 and the lumen 52. In some embodiments, the seal element 72 may prevent the priming fluid from travelling distal to the seal element 72 between the outer surface of the introducer needle 16 and the inner surface of the catheter 14.

Figure 5A:
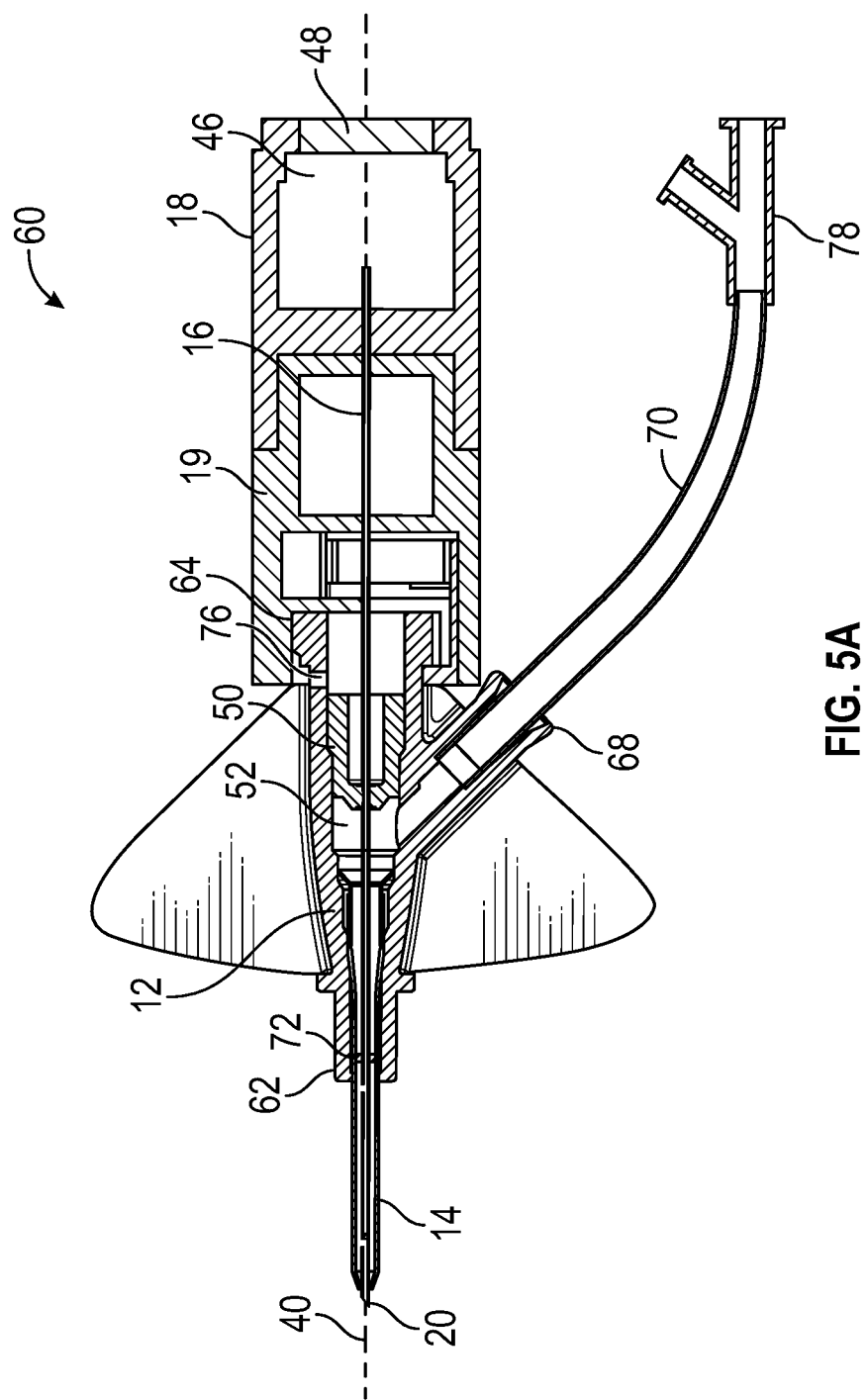
FIG. 5A is a cross-sectional view of another catheter system, according to some embodiments.
Figure 5D:
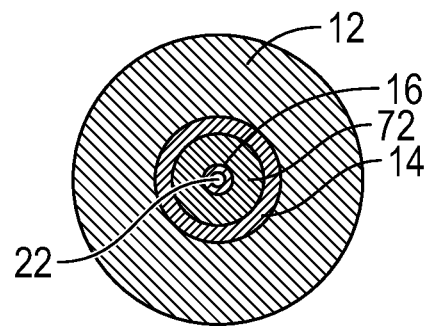
FIG. 5D is a transverse cross-sectional view at an example seal of the catheter system of FIG. 5A, according to some embodiments.
Figure 5E:
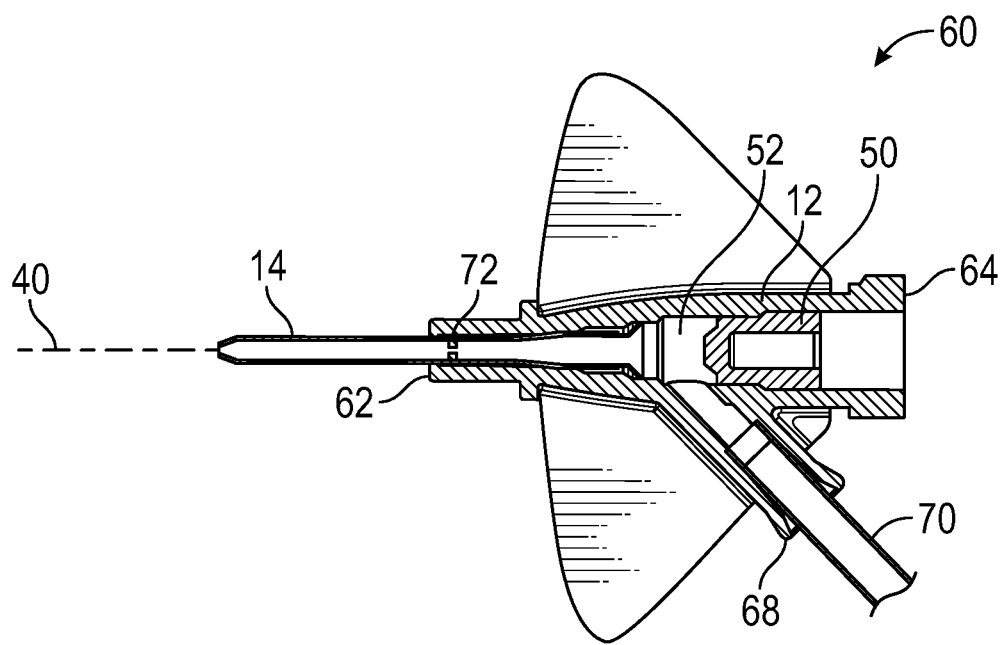
FIG. 5E is a cross-sectional view of the catheter system of FIG. 5A, illustrating an example needle assembly removed from the catheter system, according to some embodiments.
Figure 5F:
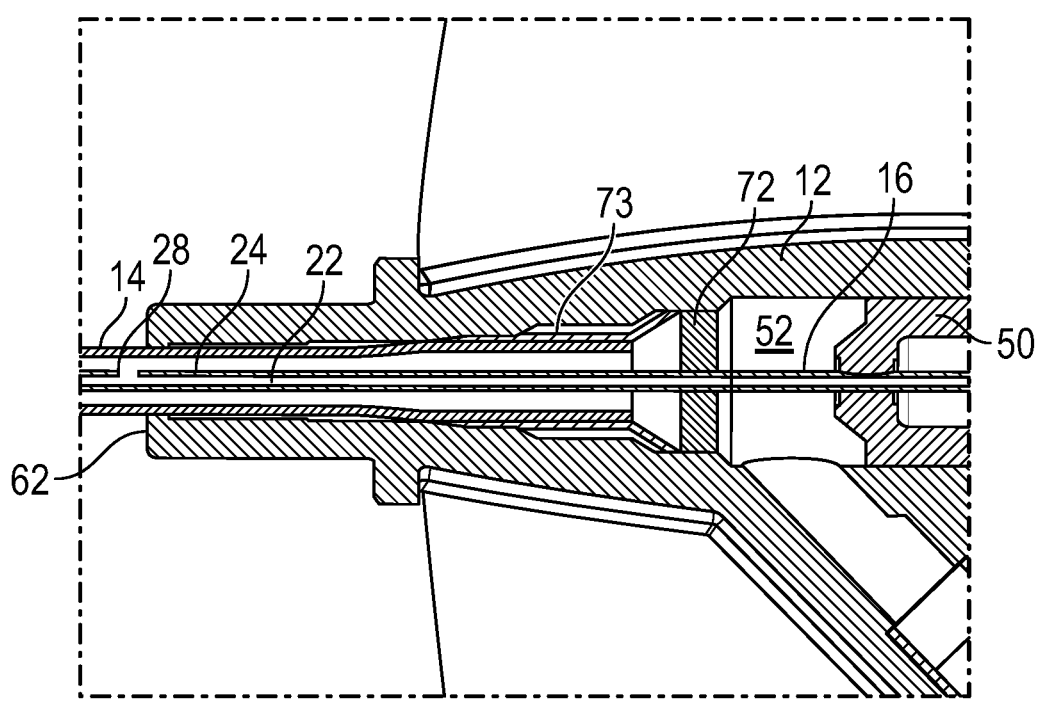
FIG. 5F is an enlarged cross-sectional view of a portion of the catheter system of FIG. 5A, illustrating an example seal element in another location, according to some embodiments.

In some embodiments, the seal element 72 may be disposed within the catheter 14 between the outer surface of the introducer needle 16 and an inner surface of the catheter 14, as illustrated, for example, in FIG. 5A. In some embodiments, the seal element 72 may be disposed proximal to the catheter 14 and within the lumen 52 distal to the junction with the side port 68 and the lumen 52, as illustrated, for example, in FIG. 5F. In some embodiments, the seal element 72 may extend through the proximal end of the catheter 14 and contact the inner surface of the catheter adapter 12 and/or a wedge 73 that secures the catheter 14 within the catheter adapter 12.

In some embodiments, the seal element 72 may prevent fluid, such as priming fluid, from travelling distal to the seal element 72 within the catheter adapter 12 and/or distal to the seal element 72 between the outer surface of the introducer needle 16 and the inner surface of the catheter 14. In some embodiments, the seal element 72 may be proximal to the second notch 28. In some embodiments, the seal element 72 may prevent the fluid from travelling distal to the seal element 72 when the introducer needle 16 extends through the seal element 72.

In some embodiments, the seal element 72 may be a separate element from the catheter adapter 12, catheter 14, the wedge 73, or another portion of the catheter system 60. In these embodiments, the seal element 72 may be coupled or positioned within the catheter system 60. In some embodiments, the seal element 72 may be engaged in an interference fit with one or more of the following: the inner surface of the catheter adapter 12, the catheter 14, or the wedge 73. In some embodiments, the seal element 72 may be constructed of metal, plastic, silicon, or any other material configured to form a seal around the introducer needle 16.

In some embodiments, the seal element 72 may be integrally formed or monolithically formed as a single unit with the catheter 14, the catheter adapter 12, or the wedge 73. In some embodiments, the seal element 72 may include a necked down or narrowed inner diameter portion of the catheter 14. In some embodiments, the seal element 72 may be annular and may surround the introducer needle 16. In some embodiments, an outer perimeter or outer circumference of the seal element 72 may contact the inner surface of one or more of the following: the catheter adapter 12, the catheter 14, and the wedge 73. In some embodiments, an inner perimeter or inner circumference of the seal element 72 may contact the outer surface of the introducer needle 16 to prevent fluid from travelling through the catheter 14. In some embodiments, the seal element 72 may include a hole extending through the seal element 72, which may include the inner perimeter or the inner circumference.

In some embodiments, the seal element 72 may not be attached to the introducer needle 16, the catheter 14, the catheter adapter 12, or the wedge 73. In some embodiments, an outer perimeter or outer circumference of the seal element 72 may be attached to the inner surface of the catheter 14. In some embodiments, the inner perimeter or inner circumference of the seal element 72 may be attached to the outer surface of the introducer needle 16 to prevent fluid from travelling through the catheter 14. In some embodiments, the seal element 72 may be constructed of a tear-able material configured to tear in response to proximal withdrawal of the introducer needle 16 with respect to the catheter adapter 12 and the catheter 14.

In some embodiments, a portion of an outer surface of the introducer needle 16 may include a groove 74. In some embodiments, the introducer needle 16 may be partially crimped to form the groove 74 such that fluid may still flow through the needle lumen 22. In some embodiments, the portion of the outer surface of the introducer needle 16 may be disposed within the septum 50. In some embodiments, the groove 74 may be configured to allow air to pass through the septum 50.

In some embodiments, the needle hub 18 may include the flash chamber 46, which may be in fluid communication with the needle lumen 22 via an opening in the proximal end of the introducer needle 16. In some embodiments, the needle hub 18 may include the gas permeable vent 48, which may be proximate the flash chamber 46.

In some embodiments, the catheter adapter 12 may include a gas permeable vent 76, which may be proximal to the septum 50. In some embodiments, the gas permeable vent 76 and/or the gas permeable vent 48 may include paper, fiber, membrane, or another material with a porosity that allow air to escape while limiting fluid from escaping. In some embodiments, the gas permeable vent 76 may be permeable to air but not blood. In some embodiments, a location of the gas permeable vent 76 may vary. In some embodiments, the gas permeable vent 76 may facilitate exit from the catheter system 60 of air travelling proximally through the groove 74. In some embodiments, the gas permeable vent 76 may be disposed within the needle shield 19, which may be disposed between the needle hub 18 and the catheter adapter 12. In some embodiments, the needle shield 19 may include any active or passive needle safety device configured to shield a sharp distal tip of the introducer needle in response to withdrawal of the introducer needle 16.

In some embodiments, a device containing priming fluid may be coupled to an adapter 78 of the catheter system 60. In some embodiments, the priming fluid may include saline. In some embodiments, the device may include a syringe or any other suitable device that may be coupled to the catheter system 60. In some embodiments, the device may be directly coupled to the adapter 78 or coupled to the adapter 78 via another connector.

In some embodiments, the adapter 78 may be coupled to the proximal end of the extension tube 70. In some embodiments, the catheter system 60 may be primed, using the device containing priming fluid, such that the priming fluid flows distally through the catheter system 60 to the seal element 72 and stops at the seal element 72. In some embodiments, the priming fluid may not flow distal to the seal element 72. In some embodiments, the catheter 14 distal to the seal element 72 may be dry and the needle lumen 22 may remain dry, while the adapter 78, the extension tube 70, the side port 68, and a portion of the lumen 52 between the seal element 72 and the septum 50 may all be primed such that any air bubbles are removed from a fluid pathway extending from the catheter adapter 12 to the adapter 78. In some embodiments, the septum 50 may prevent priming fluid from passing through the septum 50 to the proximal end 64 of the catheter adapter 12.

In some embodiments, after priming the catheter system 60 with the device containing priming fluid such that the priming fluid flows distally through the catheter system 60 to the seal element 72 and stops at the seal element 72, a clinician may insert the catheter 14 into vasculature of a patient. In some embodiments, in response to inserting the catheter 14 into the vasculature, blood may flow proximally into the needle lumen 22 at the distal tip 20, then out of the needle lumen 22 through the first notch 26 into a space between an outer surface of the introducer needle 16 and an inner surface of the catheter 14, and then into the needle lumen 22 through the second notch 28. In some embodiments, after the blood flows into the needle lumen 22 through the second notch 28, the blood may flow into the flash chamber 46.

In some embodiments, in response to observation of blood flashback by the clinician or completion of blood collection, the clinician may withdraw the introducer needle 16 in a proximal direction. In some embodiments, in response to withdrawing the introducer needle in the proximal direction, a seal formed by the seal element 72 around the introducer needle 16 may be broken such that the priming fluid joins the blood, which may be disposed in the space between the outer surface of the introducer needle 16 and the inner surface of the catheter 14 distal to the seal element 72. Thus, in some embodiments, the fluid pathway extending from the catheter adapter 12 to the adapter 78 may merge with a fluid pathway extending from the distal tip 20 into the needle lumen 22 and into the space between an outer surface of the introducer needle 16 and the inner surface of the catheter 14.

In some embodiments, in response to the seal being broken, the catheter 14 may remain in place within the vasculature for use in future infusions and/or blood collection. In some embodiments, the seal may be broken when the introducer needle 16 is withdrawn in the proximal direction such that the introducer needle 16 is removed from the seal element 72 and no longer extends through the seal element 72. In these and other embodiments, fluid may flow through the hole or middle of the seal element 72.

Figure 5G:
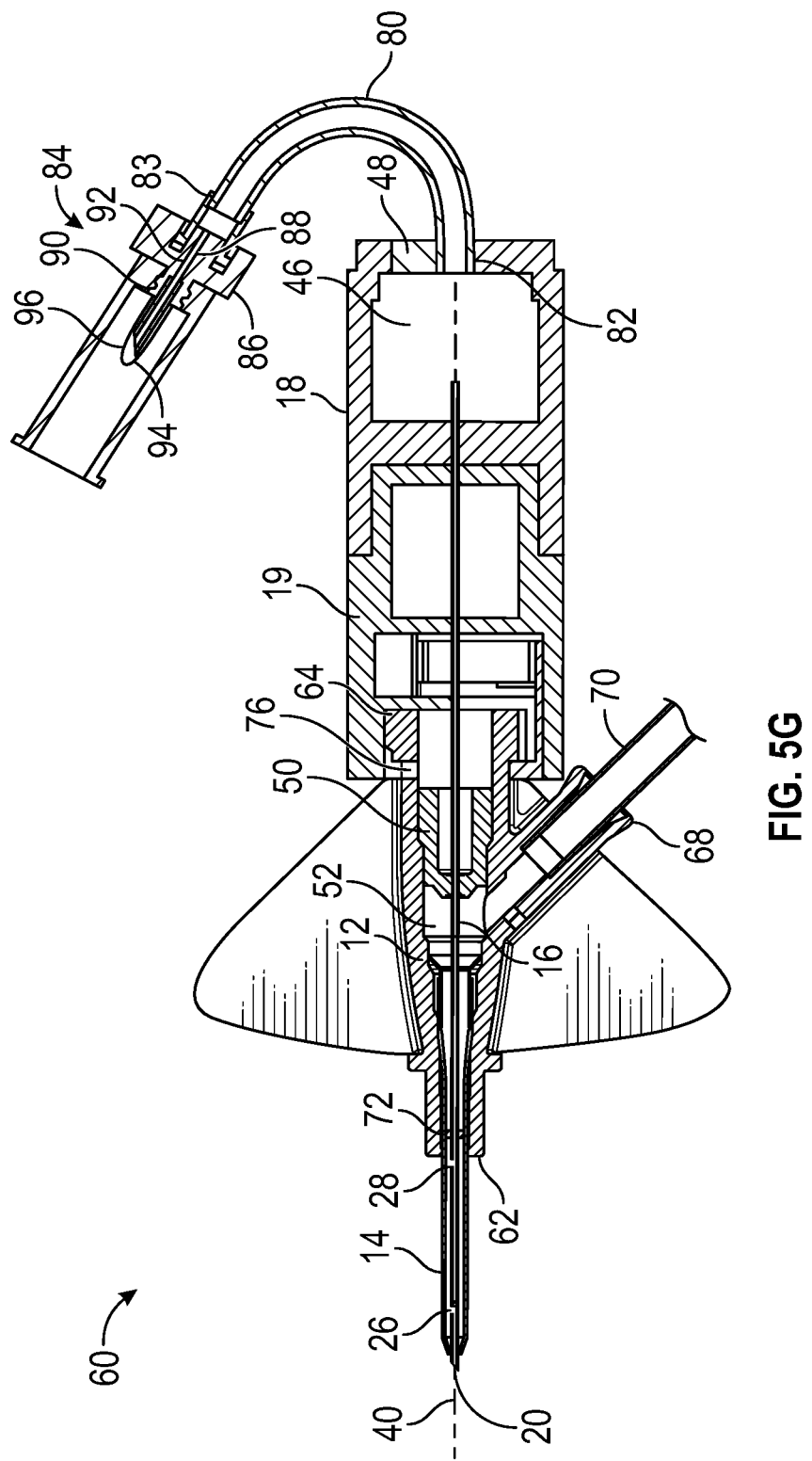
FIG. 5G is a cross-sectional view of the catheter system of FIG. 5A, illustrating another example needle hub, according to some embodiments.

Referring now to FIG. 5G, in some embodiments, the needle hub 18 may include another extension tube 80. In some embodiments, a distal end 82 of the other extension tube 80 may be in fluid communication with the flash chamber 46. In some embodiments, a proximal end 83 of the other extension tube 80 may be coupled to a holder 84 configured to receive an evacuated blood collection tube. In some embodiments, the clinician may use the catheter system 60 to collect or sample blood prior to fully removing the introducer needle 16 from the catheter adapter 12 and while the catheter 14 is inserted within the vasculature of the patient.

In some embodiments, the holder 84 may include a body 86, which may include a distal end 88, a proximal end 90, and a lumen 92 extending through the distal end 88 of the body 86 and the proximal end 90 of the body 86. In some embodiments, the distal end 88 of the body 86 may include a male port or a female port. In some embodiments, the holder 84 may include a needle 94 extending from the proximal end 90 of the body 86 and configured to receive the evacuated blood collection tube.

In some embodiments, the holder 84 may include an elastomeric sheath 96, which may be coupled to the body 86. In some embodiments, a proximal end of the needle 94 may be enveloped within the elastomeric sheath 96. In some embodiments, the elastomeric sheath 96 may include an open distal end and a closed proximal end. In some embodiments, in response to the evacuated blood collection tube pushing the elastomeric sheath 96 distally, the needle 94 may pierce the elastomeric sheath 49, and the needle 94 may insert into a cavity of the evacuated blood collection tube. In some embodiments, the holder 84 may include a BD VACUTAINER® one-use holder. In some embodiments, the holder 84 may include any suitable device configured to couple to a blood collection device or tube.

In some embodiments, the needle hub 18 may include the gas permeable vent 48, which may be proximate the flash chamber 46. In some embodiments, a location of the gas permeable vent 48 may vary. For example, the gas permeable vent 48 may be disposed near the proximal end 83 of the other extension tube 80. In some embodiments, the needle hub 18 may include a luer adapter, which may replace the other extension tube 80.

In some embodiments, in response to inserting the catheter 14 into the vasculature, blood may flow proximally into the needle lumen 22 at the distal tip 20, then out of the needle lumen 22 through the first notch 26 into a space between an outer surface of the introducer needle 16 and an inner surface of the catheter 14, and then into the needle lumen 22 through the second notch 28. In some embodiments, after the blood flows into the needle lumen 22 through the second notch 28, the blood may flow into the flash chamber 46 and/or through the other extension tube 80.

In some embodiments, the blood may then be collected in a blood collection device, such as, for example, the evacuated blood collection tube. In these and other embodiments, the seal formed by the seal element 72 may be intact.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A catheter system, comprising:
a catheter adapter, comprising a distal end, a proximal end, a lumen extending between the distal end and the proximal end, and a side port disposed between the distal end and the proximal end and in fluid communication with the lumen;
a catheter extending distally from the distal end of the catheter adapter;
an introducer needle having a wall defining a needle lumen of the introducer needle, a first notch formed through the wall, and a second notch formed through the wall, wherein the second notch is proximal to the first notch, wherein the introducer needle extends through the catheter and beyond the distal end of the catheter when the introducer needle is in an insertion position for insertion into a patient, wherein a portion of the introducer needle between the first notch and the second notch is blocked such that fluid is prevented from flowing in the needle lumen between the first notch and the second notch; and
a seal element is disposed proximal to the second notch and distal to the side port, wherein the seal element is configured to prevent a priming fluid from travelling distal to the seal element between an outer surface of the introducer needle and an inner surface of the catheter.

2. The catheter system of claim 1, further comprising a septum disposed within the lumen of the catheter adapter, wherein a portion of an outer surface of the introducer needle comprises a groove, wherein the portion of the outer surface of the introducer needle is disposed within the septum, wherein the groove is configured to allow air to pass through the septum.

3. The catheter system of claim 1, wherein the first notch and the second notch are disposed within the catheter when the introducer needle is in the insertion position.

4. The catheter system of claim 3, wherein at least a portion of the catheter is transparent or translucent.

5. The catheter system of claim 1, further comprising a needle hub, wherein a proximal end of the introducer needle is secured within the needle hub, wherein the needle hub comprises a flash chamber in fluid communication with the needle lumen.

6. The catheter system of claim 5, wherein the needle hub further comprises a gas permeable vent proximate the flash chamber.

7. The catheter system of claim 5, further comprising a needle shield disposed between the needle hub and the catheter adapter.

8. The catheter system of claim 1, further comprising a septum disposed within the lumen of the catheter adapter, wherein the catheter adapter further comprises a gas permeable vent proximal to the septum.

* * * * *